United States Patent [19]

Miller et al.

[11] Patent Number: 4,767,400

[45] Date of Patent: Aug. 30, 1988

[54] POROUS VENTRICULAR CATHETER

[75] Inventors: Sandra L. Miller, North Miami; Leonard Pinchuk, Miami, both of Fla.

[73] Assignee: Cordis Corporation, Miami, Fla.

[21] Appl. No.: 113,884

[22] Filed: Oct. 27, 1987

[51] Int. Cl.$^4$ .......................................... A61M 25/00
[52] U.S. Cl. ...................................... 604/8; 604/264; 604/280; 156/304.2
[58] Field of Search ................ 604/8, 93, 95, 264, 604/280, 266; 156/167, 92, 304.2, 309.6, 308.4

[56] References Cited

U.S. PATENT DOCUMENTS

| | | | |
|---|---|---|---|
| 3,773,034 | 11/1973 | Burns et al. | 604/95 |
| 4,377,169 | 3/1983 | Banks | 604/280 X |
| 4,475,972 | 10/1984 | Wong | 156/175 X |
| 4,507,119 | 3/1985 | Spencer | 156/304.2 |
| 4,601,724 | 7/1986 | Hooven et al. | 604/264 X |
| 4,650,466 | 3/1987 | Luther | 604/266 X |

Primary Examiner—Stephen C. Pellegrino
Attorney, Agent, or Firm—Lockwood, Alex, Fitzgibbon & Cummings

[57] ABSTRACT

A ventricular catheter and a method for making same are provided wherein the catheter comprises a tubing assembly including a porous portion and a non-porous portion. The porous portion has a high surface density of very fine pores which are substantially resistant to blockage under in vivo conditions yet allow cerebrospinal fluid to pass therethrough when the assembly is attached to a cerebrospinal fluid pressure relief system for the treatment of hydrocephalus. The porous portion is generally formed by extruding a fiber forming polymer which is wound directly onto a mandrel.

29 Claims, 2 Drawing Sheets

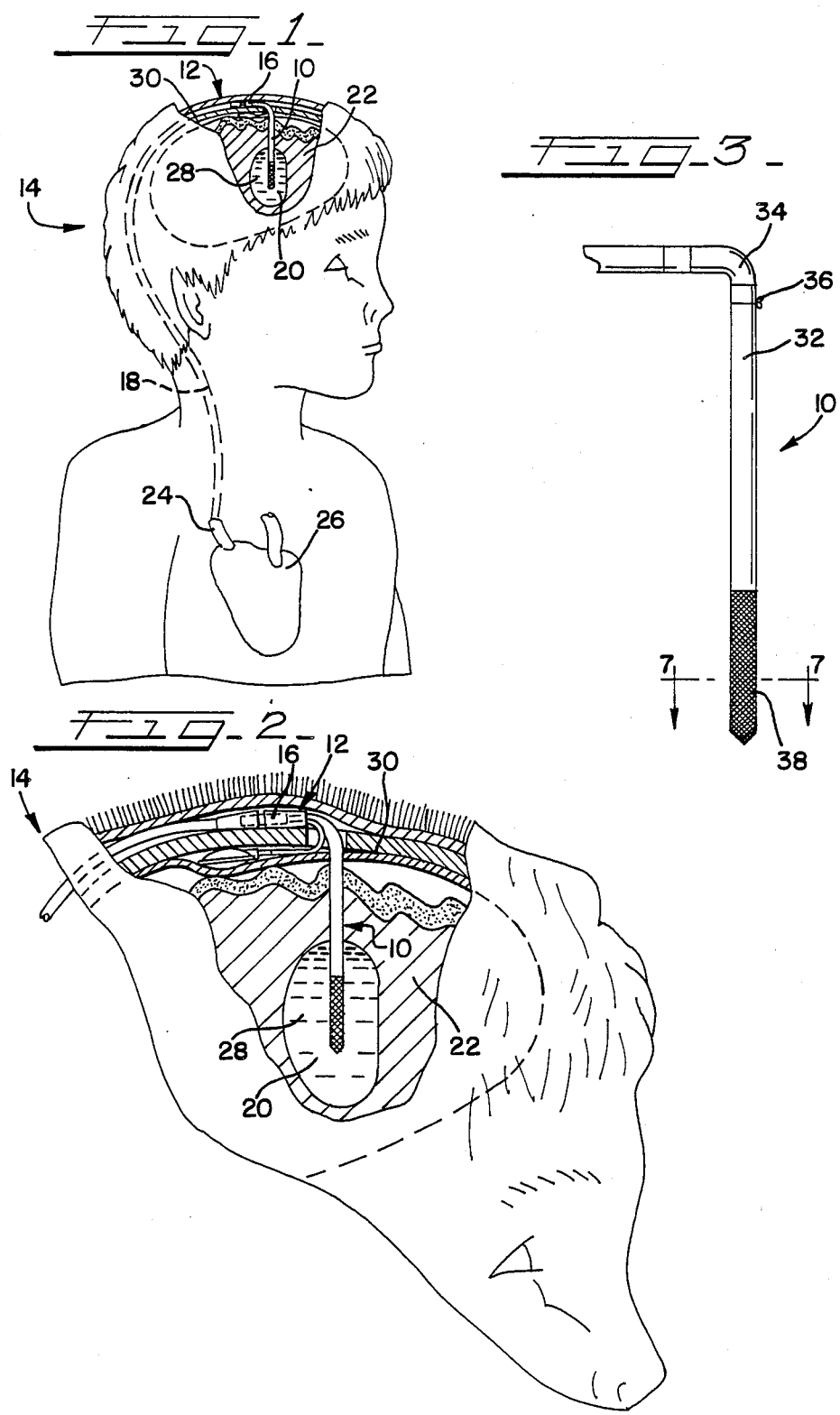

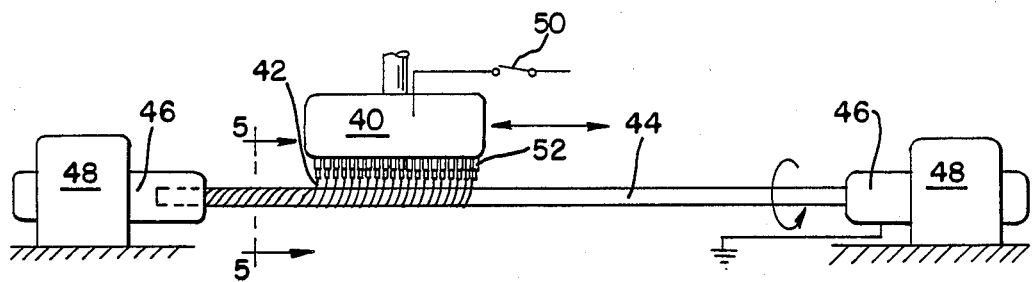
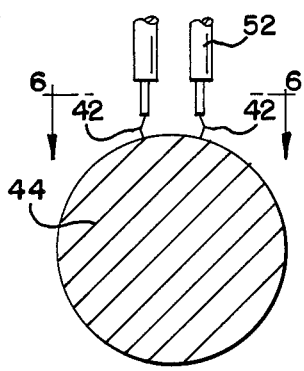
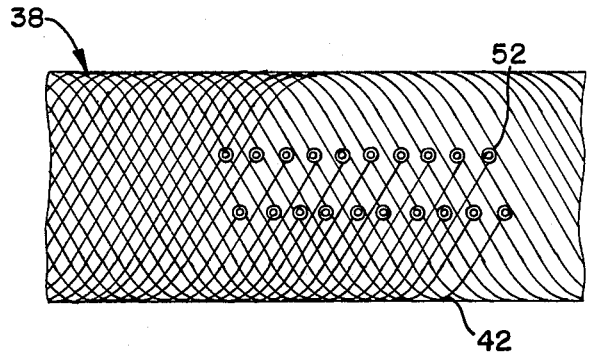
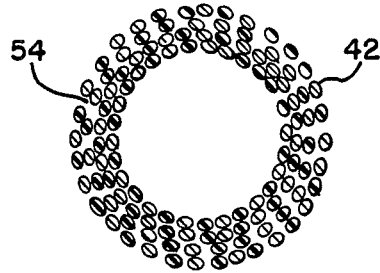
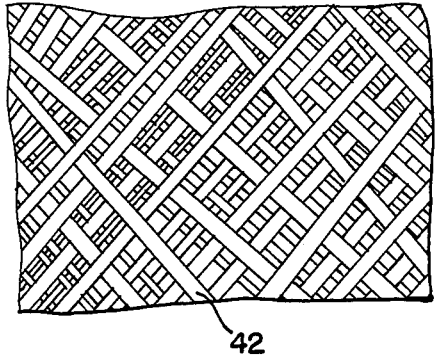

POROUS VENTRICULAR CATHETER

BACKGROUND AND DESCRIPTION OF THE INVENTION

This invention generally relates to porous tubing assemblies for catheters. More specifically, this invention relates to providing drainage catheters having an extremely fine pore structure. In an important aspect of the present invention, the extremely fine pore structure is formed by winding extruded polymer fibers onto a rotating mandrel. The wound porous portion may be bonded to a non-porous polymer tube thereby forming a tubing assembly for use in a system which drains excess cerebrospinal fluid (CSF) from a ventricle of the brain.

Systems for draining excess CSF are generally known in the art. Such systems, either for use on a temporary or substantially permanent basis, have been known and used for a number of years for the treatment of hydrocephalus. The more permanent types of systems generally include an implantable valve which allows the CSF to pass from the ventricle of the brain to a suitable drainage location within the body. Such valves are actuated by displacing an internal diaphragm or the like in response to applied pressure differentials thereby regulating the passage of CSF from the ventricular spaces, through the catheter and on to the drainage location. An example of such a valve can be found in U.S. Pat. No. 4,557,721, the disclosure of which is incorporated by reference herein.

Similar types of ventricular catheters are included in temporarily implanted intracranial drainage, monitoring, and/or injection systems which gain access to the ventricular spaces through a flexible ventricular catheter. Illustrative of such temporarily implanted systems is a system as shown in FIG. 2 of U.S. Pat.No. 4,601,724, the disclosure of which is incorporated by reference herein.

Because of the delicate nature of the brain tissue with which the catheter comes into contact, it is desirable that the tubing assembly which comprises the ventricular catheter be manufactured from flexible materials. The catheter, in addition to being flexible, contains a multitude of inlet holes or pores through which the CSF flows. A recognized problem in the art of ventricular catheters has been the problem of pore blockage caused by the ingrowth of the choroid plexus, ventricular collapse over the catheter pores, hemorrhage, and the like. Those skilled in the art have attempted to solve the problem of pore blockage in different ways. One such approach to the problem has focused on increasing the number of inlet holes or pores through which the CSF may pass into the catheter tubing. One such effort is illustrated in U.S. Pat. No. 4,601,724, mentioned above, describing a polymeric tubing assembly which includes a length of tubing having micro-orifices which are ion sputtered therethrough.

Other efforts, such as that described in U.S. Pat. Re. No. 27,310 by Hakim, have taken different approaches to the problem of pore blockage. Hakim, for example, uses a finned catheter comprising flexible membranes extending radially outward from the porous catheter tubing. These flexible membranes will bend to cover and protect the pores when contacted by tissue from the choroid plexus and the like.

The present invention provides a ventricular catheter which possesses the desired properties of small pore size with a maximal number of pores through which CSF may pass. The method and product produced thereby include providing a length of polymeric tubing assembly comprising a non-porous tubular portion bonded to a porous tubular portion. In the embodiment described herein, the porous portion typically forms roughly the distal one-third portion of the catheter tubing assembly and is bonded to the non-porous portion by heat or solvent reformation of the associated ends of the two portions. The porous portion is generally formed by extruding a fiber forming polymer, such as polyurethane, which is wound directly onto a rotating mandrel. One approach for manufacturing a porous tubular structure, suitable for use as vascular grafts, is detailed in U.S. Pat. No. 4,475,972, the disclosure of which is incorporated by reference herein.

Once the porous tubular portion and the non-porous tubular portion are bonded together, the free floating open end of the porous portion is closed, generally by heat or solvent reformation. In this manner, a tubing assembly suitable for use as a ventricular catheter is provided which includes a highly porous portion that is substantially resistant to blockage under in vivo conditions.

It is accordingly an object of the present invention to provide an improved catheter assembly.

Another object of this invention is to provide an improved method for manufacturing a tubing assembly having a porous portion formed by winding extruded polymer fibers onto a rotating mandrel.

Another object of the present invention is to provide an improved method and product produced thereby which takes advantage of the improved porosity of tubing made by winding extruded polymeric fibers onto a rotating mandrel.

These and other objects of the present invention will be apparent to those skilled in the art from the following.

BRIEF DESCRIPTION OF THE DRAWINGS

FIG. 1 is a perspective view, partially in section, of a hydrocephalus system employing a catheter tubing assembly according to the present invention and implanted within a patient.

FIG. 2 is an enlarged perspective view of the implanted hydrocephalus system of FIG. 1.

FIG. 3 is a perspective view of a ventricular catheter according to the present invention.

FIG. 4 is a generally schematic sketch illustrating a step in the manufacture of the porous portion of a ventricular catheter in accordance with this invention.

FIG. 5 is a cross-sectional view taken along the line 5—5 of FIG. 4.

FIG. 6 is a cross-sectional view along the line 6—6 of FIG. 5.

FIG. 7 is cross-sectional view of the porous portion of a tubing assembly according to the present invention and taken along the line 7—7 of FIG. 3.

FIG. 8 is a sketch of an exploded view of an external surface of a porous portion of a ventricular catheter prepared in accordance with the present invention at a magnification on the order of 150 times.

DETAILED DESCRIPTION OF THE DRAWINGS

Referring to FIGS. 1 and 2, a tubing assembly 10 according to the present invention is shown as the catheter component of an implantable cerebrospinal fluid pressure relief system 12. Such a system 12 is generally useful for the treatment of hydrocephalus by maintaining a desired predetermined intracranial pressure in a patient 14. The system 12 includes a pressure relief valve 16 and a drain catheter 18. The system 12 drains cerebrospinal fluid from a ventricle 20 of the brain 22. The cerebrospinal fluid 28 occupies the volume of the ventricle, exiting therefrom through tubing assembly 10 and passing through the pressure relief valve 16 and drain catheter 18 for discharge into a selected portion the patient's body. In the embodiment illustrated in FIG. 1, the cerebrospinal fluid is discharged into a vein 24 which terminates within the right atrium of the heart 26. Other suitable drainage locations can be selected, such as the peritoneal cavity.

Typically, pressure relief valve 16 includes means for adjusting the differential pressure threshold at which the valve 16 opens so that system 12 can be adjusted. Those skilled in the art will know that various pressure relief valve assemblies are available. Particularly suitable to the practice of the present invention are those valves which are commercially available from Cordis Corporation. The dimensions of such valves are selected to be compatible with subcutaneous implantation over the patient's cranium.

Referring now to FIG. 3, a tubing assembly 10 according to the present invention is shown. The tubing assembly 10 is typically comprised of two smaller sections. Solid or non-porous section 32 extends down through the tissue of brain 22 and into the ventricle 20. In the present embodiment, right angle connector 34 connects the tube assembly 10 to the rest of the system 12. Non-porous portion 32 may be connected to right angle connector 34 by a suture 36, as shown. However, other connecting means may be employed such as, for example, heat or solvent reformation of the associated ends of connector 34 and section 32. The use of a right angle connector 34 may be avoided as being unnecessary where there is no concern regarding pinching or kinking of the non-porous portion 32 as it exits the cranium 30 to connect with the pressure relief valve 16.

The porous portion 38 is connected to non-porous portion 32. In the particular embodiment illustrated, porous portion 38 generally comprises the distal one-third portion of the tubing assembly 10. As further described below, porous portion 38 is provided with a surface containing a maximal number of extremely fine pores or inlet holes through which CSF will pass from the ventricle 20 into the tubing assembly 10. In this manner, the problem of pore blockage by ventricular collapse, tissue ingrowth and the like, is alleviated since the structure of the porous portion 38 provides a high surface density of extremely fine pores which are resistant to blockage. Additionally, the fine pore size will allow CSF to pass therethrough while simultaneously preventing tissue ingrowth under in vivo conditions. As further explained below in reference to FIGS. 7 and 8, the pores of porous portion 38 are formed by layers of overlapping polymeric fibers. Consequently, the pore structure of the porous portion 38 is actually a complex network of circuitous channels through which CSF can flow. It is believed that the small pore size coupled with the circuitous nature of the channel network both contribute to enhance the resistance of porous portion 38 to pore blockage by tissue ingrowth and the like.

The actual manufacture of the porous portion 38 is discussed in more detail below. It is worth noting, however, that the choice of materials for manufacturing the porous portion 38 may also enhance the ability to resist tissue ingrowth. In general, materials with physical properties similar to those of polyurethanes are preferred. In this regard, polyurethanes are generally more lubricous than silastic, thereby contributing to an overall reduction in tissue adhesions when the assembly 10 is implanted in a ventricle 20. When initially manufactured, porous portion 38 is in the form of an open-ended tube. Heat or solvent reformation techniques, or their equivalents, are useful for bonding the porous portion 38 to non-porous portion 32 and for closing the free floating end of porous portion 38. In this manner, a biocompatible tubing assembly 10 is provided which is useful as a ventricular catheter and is substantially resistant to pore blockage under in vivo conditions.

Referring now to FIG. 4, an apparatus suitable for manufacturing the porous portion 38 of the present invention is illustrated. The apparatus includes a distributor 40 for achieving formation of polymeric fibers 42. The distributor 40 typically forms the fibers 42 by extrusion of a fiber-forming polymeric solution through one or more hypodermic cylinders 52. Before such fibers 42 are fully set, they are wound onto a mandrel 44 which is rotated within jaws 46. In the arrangement illustrated, the distributor 40 moves back and forth within a plane between the jaws 46, while the mandrel 44 is rotated by suitable means such as by motors 48. In this manner, the desired number of layers of polymeric fibers 42 are laid down over the mandrel 44.

Electrostatic charge generation components may be included in order to develop an electrostatic charge between the distributor 40 and the mandrel 44. Preferably, the mandrel 44 is grounded or negatively charged, while the distributor 40 is positively charged when a switch 50 or the like is closed. Alternatively, the distributor 40 can be grounded and the mandrel 44 can be positively charged. When the electrostatic charge is present, polymeric fibers 42 accelerate from the distributor 40 to the mandrel 44 faster than the acceleration achieved in the absence of the electrostatic field. Under selected conditions, such electrostatically accelerated fibers may be forced thereby into the interstices between the underlying fibers to form a surface with a desired pore size. For certain polymer/solvent solutions, under selected conditions, the application of an electrostatic charge of a predetermined magnitude may aid in obtaining a porous portion 38 with a surface that has a very small pore size. Those skilled in the art will appreciate that such results may be obtained by varying certain manufacturing parameters including the rate at which the distributor 40 moves back and forth between the jaws 46, the rate at which the mandrel 44 is rotated, the total amount of time an electrostatic charge is applied, and the particular polymer/solvent solution used to make the polymeric fibers 42. When the electrostatic field is present, adjacent polymeric fibers 42, each of which carry a like charge, tend to bow away from each other while in the gap between the cylinders 52 and the mandrel 44 as generally illustrated in FIG. 5. Distributor 40 may include any number of individual extrusion orifices or hypodermic cylinders 52.

Polymeric fibers 42, when set, form a generally cylindrical porous portion 38 which has an inside diameter substantially the same as the outside diameter of the mandrel 44. Individual fibers 42 are generally bonded to each other at the locations where the fibers intersect or otherwise contact each other. This fiber-to-fiber bonding results when the solvent-containing and partially set fibers 42 contact one another during winding and is typically facilitated by drawing the extruded fibers over other fibers lying thereunder. The actual bonding occurs upon removal of the solvent from the fibers 42, as by evaporation in air. Drawing of the fibers 42 is accomplished by selecting an appropriate speed of relative movement between the mandrel 44 and the distributor 40 thereby drawing the fibers 42 at a speed faster than the rate by which they are extruded from the distributor 40.

Winding and drawing of fibers 42 tends to occasionally result in breakage of the fibers 42. Fiber breakage can be remedied by the application of the electrostatic charge as soon as breakage occurs in order to accelerate the broken strand away from the hypodermic cylinder 52 so that the free end of the broken fiber contacts and adheres to the forming porous portion 38 which is facilitated by the rapid acceleration caused by the electrostatic force which directs the fiber 42 to the mandrel 44 and enhances the ability of the broken end to reach the porous portion 38 before the polymeric fibers 42 have set. Without application of the electrostatic field, the free end of the broken fiber typically will pendulum into the other fibers 42 causing additional fiber breakage.

The polymeric material from which the fibers 42 are extruded must be a fiber forming type of polymer. Such a polymer must be capable of being formed as a fiber when extruded through a fine orifice, such as the hypodermic cylinders 52, and into the air. Polyamides such as the nylons and regenerated celulose products such as the rayons are fiber forming. As a general class of polymers, the polyurethanes tend to possess the physical properties desirable for the manufacture of ventricular catheters. Segmented polyurethanes, however, are typically not looked upon as being fiber forming in air, and when extruded they tend to exhibit excessive breakage. Nevertheless, polyurethanes of the type that are fiber forming are generally preferred.

Referring now to FIG. 7, illustration is made of the structure of porous portion 38 viewed at a cross-section along the 7—7 line of FIG. 3. Fibers 42 form distinct layers as determined by the number of passes of the distributor 40 over the mandrel 44. The overall thickness of the wall of porous portion 38 is dependent both on the number of layers and on the thickness on the extruded fibers 42.

The conditions under which the porous portion 38 is manufactured can be varied to achieve different effects. In the present application, conditions should be such so that the porous portion 38 will allow the passage of CSF therethrough while also creating pores 54 which are small enough to resist in vivo tissue ingrowth. For some polymers, such results can generally be obtained by formulation of the polymer solution to have a high solvent content and by extruding the polymer under electrostatic conditions. In this manner, the fibers 42 are accelerated onto the mandrel 44 at a high velocity and draw down ratio and impact on the mandrel 44 before significant solvent evaporation can occur. Electrostatic acceleration generally results in a flattening of the fibers 42 while simultaneously forcing these fibers 42 into the interstices between the underlying fibers.

Those skilled in the art will appreciate that the exact manufacturing conditions, such as the exact length of time during which the electrostatic charge is applied, will depend on the polymer/solvent solution employed as well as the apparatus utilized in extruding and winding the fibers 42. In certain applications, it may be desirable to minimize or avoid the use of an electrostatic charge. In such cases, the size and shape of the pores may be controlled by the angle subtended by the fibers 42 with respect to the mandrel 44 as well as the thickness of the extruded fibers 42. The use of an electrostatic charge, as is true of all other manufacturing parameters, will require some degree of judgment on the part of the operator in manufacturing the porous portion 38. Although the use of such a charge may be desirable in some instances, it may be totally inappropriate in other situations. Therefore, as indicated above, no single manufacturing variable is controlling. Rather, each such manufacturing variable must be considered in relation to the other manufacturing variables. For example, the relative speed at which the distributor 40 moves back and forth, the use of and the need for an electrostatic field, and the like, will depend on the particular polymer/solvent solution used to the make the fibers 42 as well as on the various other manufacturing parameters.

In the embodiment disclosed herein, the preferred wall thickness of the tubing assembly 10 is typically 0.025 inch. The size of pores 54 of porous portion 38 should be such that CSF can flow into the tubing assembly 10 while the choroid plexus and other blocking means are excluded. FIG. 8 shows a magnified section of a surface of porous portion 38 illustrating how fibers 42 form a network of interstitial pores through which CSF can flow.

It will be understood that the embodiments of the present invention which have been described are illustrative of the applications of the principles of the present invention. Numerous modifications may be made by those skilled in the art without departing the true spirit and scope of the invention as defined by the following claims.

We claim:

1. A method for manufacturing a biocompatible ventricular catheter, comprising:
   providing a non-porous portion of polymeric tubing having a selected outer diameter;
   providing a porous portion of polymeric tubing having a selected outer diameter, said porous portion providing step including extruding a fiber forming biocompatible polymeric material through an orifice to form an elongated fiber, winding said fiber on a mandrel such that the continuous fiber forms a plurality of windings, said windings defining a non-woven cylinder having overlying fibers that contact one another to form a porous outer surface that is resistant to in vivo blockage, and removing said non-woven cylinder from said mandrel;
   bonding an open end of said non-porous portion to an open end of said porous portion; and
   closing and sealing the remaining open end of said porous portion.

2. The method of claim 1, wherein said fiber-forming biocompatible polymeric material is a viscous solution of polyurethane fiber-forming material and solvent that produces fiber-to-fiber bonding between overlying fibers during said winding procedure by removal of said solvent therefrom.

3. The method of claim 1, wherein said fiber-forming biocompatible polymeric material is a viscous solution of polymeric fiber-forming material and solvent that produces fiber-to-fiber bonding between overlying fibers during said winding procedure by removal of said solvent therefrom.

4. The method of claim 1, wherein said extruding and winding procedure includes applying an electrostatic charge between said extrusion orifice and said mandrel, said electrostatic charge accelerating said elongated fiber onto said mandrel.

5. The method of claim 1, wherein said winding procedure includes providing fiber-to-fiber bonding between overlying fibers.

6. The method of claim 1, wherein said bonding step includes reformation of said open end of said porous portion and said open end of said non-porous portion by applying heat, a solvent or a combination of heat and a solvent.

7. The method of claim 1, wherein said closing and sealing step includes reformation of said remaining opened end of said porous portion by applying heat, a solvent or a combination of heat and a solvent.

8. The method of claim 1, wherein said outer diameter of said non-porous portion is substantially equal to said outer diameter of said porous portion.

9. A ventricular catheter made by a process, comprising:
providing a non-porous portion of polymeric tubing having a selected outer diameter;
providing a porous portion of polymeric tubing having a selected outer diameter, said porous portion providing step including extruding a fiber forming biocompatible polymeric material through an orifice to form an elongated fiber, winding said fiber on a mandrel such that the continuous fiber forms a plurality of windings, said windings defining a non-woven cylinder having overlying fibers that contact one another to form a porous outer surface that is resistant to blockage thereof after the tubing assembly is implanted, and removing said non-woven cylinder from said mandrel;
bonding an open end of said non-porous portion to an open end of said porous portion; and
closing and sealing the remaining opened end of said porous portion.

10. The tubing assembly according to claim 9, wherein said polymeric material of the porous portion is polyurethane.

11. The tubing assembly according to claim 9, wherein said porous portion defines the distal approximate one-third portion of said tubing assembly.

12. The tubing assembly according to claim 9, wherein said porous portion and said non-porous portion are bonded together by reformation of the associated ends of said porous and non-porous portions by applying heat, a solvent, or a combination of heat and a solvent.

13. The tubing assembly according to claim 9, wherein said closing and sealing step includes reformation of said remaining open end of said porous portion by applying heat, a solvent, or a combination of heat and a solvent.

14. The tubing assembly of claim 9, wherein said porous portion has a high surface density of very fine pores, said pores allowing cerebrospinal fluid to pass therethrough while resisting blockage under in vivo conditions.

15. The tubing assembly of claim 9, wherein said extruding and winding procedure includes applying an electrostatic charge between said extrusion orifice and said mandrel, said electrostatic charge accelerating the elongated fiber onto the mandrel.

16. An implantable cerebrospinal fluid pressure relief system including a hydrocephalus pressure relief valve, draining means and a ventricular catheter, wherein the improvement comprises said ventricular catheter being made by a process including:
providing a non-porous portion of polymeric tubing having a selected outer diameter;
providing a porous portion of polymeric tubing having a selected outer diameter, said porous. portion providing step including extruding a fiber forming biocompatible polymeric material through an orifice to form an elongated fiber, winding said fiber on a mandrel such that the continuous fiber forms a plurality of windings, said windings defining a non-woven cylinder having overlying fibers that contact one another to form a porous outer surface that is resistant to in vivo blockage, and removing said non-woven cylinder from said mandrel;
bonding an open end of said non-porous portion to an open end of said porous portion; and
closing and sealing the remaining open end of said porous portion.

17. The implantable system according to claim 16, wherein said porous portion of polymeric tubing and said non-porous portion of polymeric tubing are made from polyurethane.

18. The implantable system according to claim 16, wherein said porous portion defines the distal approximate one-third portion of said ventricular catheter.

19. The implantable system according to claim 16, wherein said porous portion has a high surface density of very fine pores, said pores allowing cerebrospinal fluid to pass therethrough while resisting pore blockage under in vivo conditions.

20. The implantable system according to claim 16, wherein said porous portion and said non-porous portion are bonded together by reformation of the associated ends thereof by heat, a solvent, or a combination of heat and a solvent.

21. The implantable system according to claim 16, wherein said closing and sealing steps include reformation of said remaining open end of said porous portion by heat, a solvent, or a combination of heat and a solvent.

22. The implantable system according to claim 16, wherein said outer diameter of said non-porous portion is substantially equal to said outer diameter of said porous portion.

23. The implantable system according to claim 16, wherein said porous portion allows the passage of cerebrospinal fluid therethrough while simultaneously being resistant to blockage when implanted in a patient.

24. The implantable system according to claim 16, wherein said extruding and winding procedure includes applying an electrostatic charge between said extrusion orifice and said mandrel, said electrostatic charge accelerating the elongated fiber onto the mandrel.

25. An implantable cerebrospinal fluid pressure relief system including cerebrospinal fluid draining means, and a ventricular catheter, said ventricular catheter comprising:
a non-porous portion of biocompatible polymeric tubing having a selected outer diameter;
a porous portion of biocompatible polymeric tubing having a selected outer diameter, said porous portion consisting of a non-woven cylinder of overlying polymeric fibers that contact one another to form a porous outer surface, said non-woven cylinder porous portion being bonded to said non-porous tubing portion; and one of the ends of said porous portion is closed and sealed 26. The tubing assembly of claim 25, wherein said porous portions and said non-porous portions are bonded together by reformation of the associated open ends thereof by heat, a solvent, or a combination of heat and a solvent.

27. The tubing assembly of claim 25, wherein said outer surface of said porous portion includes a high density of very fine pores which allow fluid to pass therethrough while simultaneously being resistant to blockage under in vivo conditions.

28. The tubing assembly of claim 25, wherein said porous portion is made from a polyurethane.

29. The tubing assembly of claim 25, wherein said cerebrospinal fluid draining means includes a hydrocephalus pressure relief valve.

* * * * *